US008937756B2

(12) United States Patent
Sebesta et al.

(10) Patent No.: US 8,937,756 B2
(45) Date of Patent: Jan. 20, 2015

(54) METHOD FOR AND USE OF DIGITAL HOLOGRAPHIC MICROSCOPY AND IMAGING ON LABELLED CELL SAMPLES

(75) Inventors: Mikael Sebesta, Dalby (SE); Kersti Alm, Lund (SE); Anders Långberg, Trelleborg (SE); Anna Mölder, Blentarp (SE); Johan Persson, Malmö (SE); Lennart Gisselsson, Lund (SE)

(73) Assignee: Phase Holographic Imaging PHI AB, Lund (SE)

( * ) Notice: Subject to any disclaimer, the term of this patent is extended or adjusted under 35 U.S.C. 154(b) by 0 days.

(21) Appl. No.: 13/521,701

(22) PCT Filed: Feb. 7, 2011

(86) PCT No.: PCT/SE2011/050139
§ 371 (c)(1),
(2), (4) Date: Oct. 23, 2012

(87) PCT Pub. No.: WO2011/099925
PCT Pub. Date: Aug. 18, 2011

(65) Prior Publication Data
US 2013/0230864 A1    Sep. 5, 2013

Related U.S. Application Data

(60) Provisional application No. 61/302,867, filed on Feb. 9, 2010.

(30) Foreign Application Priority Data

Feb. 9, 2010   (SE) .................................... 1050131-0

(51) Int. Cl.
*G03H 1/00*   (2006.01)
*G03H 1/04*   (2006.01)
*G02B 21/00*  (2006.01)
*C12Q 1/02*   (2006.01)
*G03H 1/08*   (2006.01)

(52) U.S. Cl.
CPC .............. *C12Q 1/02* (2013.01); *G03H 2222/31* (2013.01); *G03H 1/0866* (2013.01); *G03H 1/0443* (2013.01); *G03H 2210/12* (2013.01); *G03H 2222/13* (2013.01); *G02B 21/00* (2013.01); *G03H 2001/0471* (2013.01); *G03H 2001/005* (2013.01); *G03H 2210/63* (2013.01); *G03H 2001/0033* (2013.01)
USPC .............. 359/1; 359/10; 356/457; 422/82.05; 435/7.1; 436/518

(58) Field of Classification Search
CPC .................. G03H 2001/0471; G03H 2210/10; G01B 9/02; G01B 9/02047; G01B 9/021; G01N 21/41; G01N 33/58
See application file for complete search history.

(56) References Cited

U.S. PATENT DOCUMENTS

| | | |
|---|---|---|
| 6,262,818 B1 | 7/2001 | Cuche et al. ........................ 359/9 |
| 2004/0156098 A1 | 8/2004 | Dubois et al. ................... 359/368 |
| 2005/0036181 A1* | 2/2005 | Marquet et al. ................... 359/15 |
| 2005/0130163 A1* | 6/2005 | Smith et al. ......................... 435/6 |
| 2006/0256676 A1* | 11/2006 | Nolte et al. .................... 369/47.1 |
| 2009/0067018 A1* | 3/2009 | Pu et al. ............................. 359/1 |
| 2009/0128825 A1 | 5/2009 | Akcakir ......................... 356/457 |

FOREIGN PATENT DOCUMENTS

| | | |
|---|---|---|
| WO | WO 2006/090320 | 8/2006 |
| WO | WO 2007/073345 | 6/2007 |
| WO | WO 2009/154558 | 12/2009 |

OTHER PUBLICATIONS

Luo et al., Laser-induced fluorescence imaging of subsurface tissue structures with a volume holographic spatial-spectral imaging system, Optics Letters, vol. 33, No. 18, published Sep. 11, 2008, pp. 2098-2100.*
Hsieh et al., Three-dimensional harmonic holographic microcopy using nanoparticles as probes for cell imaging, Optics Express, vol. 17, No. 4, published Feb. 11, 2009, pp. 2880-2891.*
Schlammandinger, J., et al. (2005) "Birefringence of cells grown in vitro and of mitotic chromosomes after staining with picrosiruius red" Brazilian Journal of Morphology Sciences, 22(2):105-111.
Supplementary European Search Report for EP Application No. 11 74 2554 dated Jun. 24, 2013.
International Preliminary Report on Patentability for PCT/SE2011/050139 mailed on Aug. 14, 2012.
Gutzler, T., et al. (2010) "High resolution, wide-field microscopic imaging of biological tissue by coherent synthesis of Fourier holograms" Photonics Society Winter Topicals Meeting Series (WTM), IEEE, pp. 68-69.
Mo, X., et al. (2009) "Application of color digital holographic microscopy for analysis of stained tissue sections" Advanced Microscopy Techniques, Progress in Biomedical Optics and Imaging, Proceedings of SPIE, vol. 7367, pp. 736718-1.
Warnasooriya, N., et al. (2010) "Imaging gold nanoparticles in living cell environments using heterodyne digital holographic microscopy" Optics Express, vol. 18, No. 5, pp. 3264-3273.
International Search Report for PCT/SE2011/050139 dated Apr. 26, 2011.

* cited by examiner

*Primary Examiner* — Melanie Y Brown
*Assistant Examiner* — Rebecca Martinez
(74) *Attorney, Agent, or Firm* — Harness, Dickey & Pierce, P.L.C.

(57) ABSTRACT

The present invention relates to use of a digital holographic microscopy and imaging setup and a method of digital holographic microscopy and imaging for detecting molecules or structures stained or labelled to at least one cell or conjugated to antibodies which are bound either directly to said at least one cell or indirectly via another or several antibodies in a chain bound to said at least one cell.

6 Claims, No Drawings

METHOD FOR AND USE OF DIGITAL HOLOGRAPHIC MICROSCOPY AND IMAGING ON LABELLED CELL SAMPLES

PRIORITY STATEMENT

This application is a national phase under 35 U.S.C. §371 of PCT International Application No. PCT/SE2011/050139 which has an International filing date of 7 Feb. 2011, which claims priority under 35 U.S.C. §119 to Swedish Patent Application No. 1050131-0, filed on 9 Feb. 2010, and to U.S. Provisional Patent Application No. 61/302,867 filed on 9 Feb. 2010. The contents of each application recited above are incorporated herein by reference in their entirety.

TECHNICAL FIELD OF THE INVENTION

The present invention relates to a method for and use of digital holographic microscopy and imaging for detecting molecules or structures stained or labelled to at least one cell or conjugated to antibodies which are bound either directly to said at least one cell or indirectly via another or several anti-bodies in a chain bound to said at least one cell.

BACKGROUND ART

There exists a never ending demand for additional and more accurate information about biological objects, such as cells, in humans, animals, plants and other organisms. Cells are very thin and contain only very few structures that are easily identifiable using a light microscope. Several different methods have been developed to make cells and cell structures more visible. Many of the methods include stains that colour the entire cell or stains that colour only certain cell structures. These stains can be fluorescent or non-fluorescent. An example is trypan blue which is a widely used non-fluorescent stain that colours the entire cell blue. Trypan blue is only used for dead cells. The exact methods used to stain the cells vary as different stains have different properties. A rather recent labelling method is to induce the cell itself to produce a fluorescent substance such as green fluorescent protein (GFP). This labelling can be either very selective, showing a specific cell structure, or non-selective, showing the entire cell. Another widely used method called immuno-labelling is to label the cells using antibodies. Antibodies are proteins that are found in the body fluids of vertebrates. Antibodies bind to substances and particles, e.g. bacteria or viruses, which are thus recognized as foreign objects, and they target very specific structures. This is useful for biological and medical research as antibodies can be used to identify very specific small structures in a cell or parts of a cell. Antibodies are very difficult to detect, but they can be conjugated to a wide array of different molecules or structures that make them clearly visible. Different antibody conjugates are suited for different detection methods such as light microscopy, electron microscopy, spectrometry or radioactivity measurements. Conjugated antibodies can be used to bind directly to a target. If a stronger signal is needed, the signal can be amplified by first allowing unlabelled antibodies to bind to the target, and then allow a second set of conjugated antibodies to bind to the first set of non-conjugated antibodies. The first set of antibodies is called primary anti-bodies and the second set is called secondary antibodies. Further layers of antibodies can be used if the signal needs more amplification.

Different types of stains, labels and antibody conjugates have different light-related characteristics such as the ability to absorb light at several or a few wavelengths, to emit light at certain wavelengths, to disperse light or to polarize light. These different characteristics allow the stains to show as colouring or fluorescence when using a light microscope, a phase contrast microscope, a fluorescence microscope or a flow cytometer. The stains, labels or conjugates can also be measured using e.g. a spectrophotometer or a fluorescence plate reader.

Examples of antibody conjugates which render absorption differences are quantum dots, plastic balls, glass beads and semiconductors. Examples of antibody conjugates which scatter light or polarize it are dynabeads, gold particles, nano crystals or magnetic beads.

Digital holographic microscopy enables the study of living cells without the need for markers. In WO2009/154558, which describes an observation vessel for digital holographic microscopy and a method for digital holographic microscopy by use of said vessel, there is disclosed that digital holographic microscopy enables studies of living cells without the need for markers or stains. Fact is that digital holographic microscopy and imaging renders monochromatic images, which up til now have implied that such technology has not been interesting for analysing labelled or stained cell samples. The use of markers is increasing, so also the interest in such markers and the possible applications in relation thereto for different sample analysis.

One way to study cells by means of digital holographic microscopy is disclosed in WO 2007/073345, where a method for analyzing a stage of development of cells and a device for enablement of the analysis is disclosed.

As mentioned above, another method for studying cells by means of digital holographic microscopy is disclosed in WO2009/154558.

As said above, the technology of digital holographic microscopy and imaging renders monochromatic images. This implies that this technology, e.g. defined in the inventions disclosed in WO 2007/073345 and WO2009/154558, has not been of interest in relation to use of labelling and staining of cell samples.

SUMMARY OF THE INVENTION

The present invention is directed to use of a digital holographic microscopy and imaging setup for detecting molecules or structures stained or labelled to at least one cell or conjugated to antibodies which are bound either directly to said at least one cell or indirectly via another or several antibodies in a chain bound to said at least one cell.

Moreover, the present invention also refers to a method for detecting such molecules or structures, said method comprising the steps of performing digital holographic microscopy and imaging on a cell sample by a) creating at least one object beam and at least one reference beam of light, where said at least one object beam and said at least one reference beam are mutually coherent;

b) exposing said cell sample to said at least one object beam;

c) superimposing said at least one object beam that has passed through said cell sample with said at least one reference beam and thereby creating an interference pattern;

d) detecting said interference pattern, called hologram;

e) reconstructing phase and/or amplitude information of object wavefront from said interference pattern; and f) constructing at least one cell analysis image for detection of molecules or structures stained or labelled to at least one cell or conjugated to antibodies which are bound either directly to said at least one cell or indirectly via another or several antibodies in a chain bound to said at least one cell.

DETAILED DESCRIPTION OF THE INVENTION

In digital holography microscopy, several focal planes may be studied without having to mechanically set the microscope in relation to the different focal planes. Instead the different focal planes may be studied by processing the achieved data. Thereby, 3-dimensional images may be obtained. In particular, this method achieves a low rate of undesired interference, low levels of noise, accurate phase and amplitude information about a cell sample as well as high-resolution holographic images of the cell sample.

In one embodiment of the method according to the present invention, the mutually coherent at least one object beam and at least one reference beam of light are created by dividing a light beam originating from a coherent light source into two beams e.g. by means of a beam splitter. The light beam originating from a coherent light source may be a laser beam. The laser beam may originate from any kind of laser source, such as a He—Ne or a diode laser. Preferably a diode laser is used. The laser source may be linearly polarized.

The object beam and the reference beam are mutually coherent, which implies that they have the same wavelength and exhibit a constant phase relationship during the course of time.

The object beam is passed through the cell sample. The reference beam is left unaffected by the cell sample, since the reference beam is guided another path than the object beam, e.g. by means of beam splitters, mirrors and/or fibre optics.

The object beam has a known wavefront before passing through the cell sample. When the object beam passes through the at least one cell sample, the cell sample substantially does not absorb any light, but the light that travels through the cell sample will experience a difference in the optical path length compared to the surrounding medium. The wavefront that emerges from the cell sample, the object wavefront, will thus be phase shifted. Naturally, also the reference beam has a known wavefront. The optical path length is defined as the physical/geometrical thickness multiplied with the refractive index.

In one embodiment of the method according to the present invention, the superimposing of the at least one object beam that has passed through the cell sample and the at least one reference beam is achieved by bringing the two beams together e.g. by means of another beam splitter. This superimposition gives rise to an interference pattern, which for example includes information about the object wavefront that is affected by the at least one cell sample.

In one embodiment of the method according to the present invention, the interference pattern is detected by means of a digital sensor, such as a CCD or a CMOS. The detected interference pattern is called a hologram.

In order to superimpose the at least one object beam that has passed through the cell sample and the at least one reference beam and thereby creating an interference pattern and to detect the interference pattern for example a Fourier setup or a Fresnel setup may be used. Preferably a Fresnel setup is used. The difference between a Fourier setup and a Fresnel setup may be described as a difference in the optical configuration implying that a certain condition is fulfilled which makes an approximation, e.g. a Fresnel approximation, applicable in the reconstruction algorithm. This approximation simplifies the process of image reconstruction. In case of a Fresnel setup, the condition is that the distance between the object and the sensor is large compared to the size of the object and the size of the sensor. This is achieved by use of a microscope objective that collects the scattered light from the object and directs it to the sensor in an almost parallel light beam. This creates a virtual object that is positioned far away from the sensor.

From the detected interference pattern phase and/or amplitude information of the object wavefront is reconstructed. The reconstruction is carried out by means of any common numerical reconstruction process such as Fourier transform reconstruction or convolution reconstruction. The amplitude information may be used to set the focal plane of interest. The reconstructed information may for example be used to obtain an image in two dimensions or a 3D representation of the studied cell sample.

As an alternative for creating one object beam and one reference beam, in-line digital holography may be used. It is obvious for a person skilled in the art how to modify the method of the present invention in order to use inline digital holography, when studying this specification.

The obtained image is further used in image processing conducted by a computer in order to determine useful information about the studied object, such as shape, volume and optical density.

Several obtained images may also be further used in image processing in order to determine additional useful information about the studied object, such as changes in shape, volume and optical density.

SPECIFIC EMBODIMENTS OF THE INVENTION

In some embodiments, the molecules or structures or the antibodies are bound to the cell surface of said at least one cell. This further improves the lenience of the present invention, since the risk of harming the cell is decreased.

In some embodiments of the use of a digital holographic microscopy and imaging setup according to the present invention, the molecules or structures have a light absorption peak within a specific wavelength range and/or shift the polarization direction of a beam of light used in the digital holographic microscopy and imaging setup. By using molecules or structures that have a light absorption peak within a specific wavelength range the molecules or structures may be detected. By using molecules or structures that shift the polarization direction of a beam of light the molecules or structures may be detected.

According to one specific embodiment of the use of a digital holographic microscopy and imaging setup according to the present invention, more than one type of molecules or structures are stained or labelled to at least one cell at the same place or places of said cell or conjugated to the same type of antibodies which are bound either directly to said at least one cell or indirectly via another or several antibodies in a chain bound to said at least one cell, and wherein at least one of the molecules or structures have a light absorption peak within a specific wavelength range and at least one of the molecules or structures shift the polarization direction of a beam of light used in the digital holographic microscopy and imaging setup. According to this embodiment, molecules or structures having the ability to absorb light with a peak within a specific wavelength range are used together with molecules or structures having the ability to shift the polarization direction, i.e. two different types of molecules or structures are used. By combining these characteristics, it is possible to obtain both images created from light with different wavelengths and images created by different polarization directions. When having both these kinds of images, the certainty of the detection of the cell the molecules or structures are bound to is increased.

In some embodiments of the use of a digital holographic microscopy and imaging setup according to the present invention, the specific molecules or structures used have a light absorption peak within a specific wavelength range and shift the polarization direction of a beam of light used in the digital holographic microscopy and imaging setup. In these embodiments molecules or structures having both the ability to absorb light with a peak within a specific wavelength range and to shift the polarization direction are used, i.e. one type of molecules or structures are used. As said above, by combining these characteristics, it is possible to obtain both images created from light with different wavelengths and images created by different polarization directions. When having both these kinds of images, the certainty of the detection of the molecules or structures is increased and thus certainty of the detection of the cell the molecules or structures are bound to is increased.

In some embodiments of the use of a digital holographic microscopy and imaging setup according to the present invention, the digital holographic microscopy and imaging setup is arranged to expose said molecules or structures with light having at least two different wavelengths in comparison to one another. By exposing the molecules or structures with light having at least two different wavelengths the reliability of the detection of the molecules or structures is increased.

In some embodiments of the use of a digital holographic microscopy and imaging setup according to the present invention, the digital holographic microscopy and imaging setup is arranged to shift the polarization direction of at least one object beam of light and/or of at least one reference beam of light used in the digital holographic microscopy and imaging setup. By shifting the polarization direction of an object beam and/or a reference beam of light the reliability of the detection of the molecules or structures is increased.

Preferably, the polarization directions of the at least one object beam and the at least one reference beam are shifted so that the polarization directions obtained are perpendicular or substantially perpendicular to each other. From the beginning, the polarization directions of the at least one reference beam and of the at least one object beam are normally the same. However, for the detection of molecules or structure which have the ability to change the polarization directions of light in a randomised way, the polarization directions of the at least one object beam in relation to the at least one reference beam should be shifted towards being perpendicular to each other. According to this embodiment of the present invention, the angle of the polarization direction of the at least one object beam in relation to the at least one reference beam does not have to be exactly 90 or 270 degrees to be able to detect molecules or structures that shift the polarization direction of light or change the polarization direction in a randomized way. However, as the angle is shifted towards having a perpendicular polarization direction of the at least one object beam in relation to the polarization direction of the at least one reference beam, it will be easier to detect the molecules and structures. An angle of less than 90 degrees or more than 90 degrees will also work according to the present invention, such as an angle of e.g. between 75-89 degrees or e.g. 91-105 degrees, i.e. or 255-269 degrees or 271-285 degrees. However, at an angle of 90 or 270 degrees the only interference pattern detectable is from the molecules or structures which themselves change the polarization direction in a randomized way.

In relation to the method according to the present invention, according to one specific embodiment, two or more wavelengths are used, wherein the specific molecules or structures used have a light absorption peak in a wavelength range covering at least one, but not all of the two or more wavelengths, and wherein the steps a) to f) are performed for each of the used wavelengths, thereby enabling comparison of said one and same at least one cell in images obtained in step f) and created from light with different wavelengths.

By using two or more wavelengths it is possible to increase the reliability of the method according to the present invention. If molecules or structures are used which have a light absorption peak in a specific wavelength range, it is possible to use at least one wavelength within that range and one outside that range. As such, the actual detection of the molecules or structures may be determined.

Moreover, by using at least two wavelengths and produce an image for each of the used wavelengths it is possible to compare the obtained images. Since the molecules or structures used have a light absorption peak within a wavelength range covering at least one of the used wavelengths and not one other used wavelength, the molecules or structures will affect at least one of the images and not affect at least one other image. By comparing an affected and an unaffected image, the molecules or structures are detected.

One way to carry out the method involving two or more wavelengths is to first perform steps a) to f) for one of the used wavelengths and then perform steps a) to f) for one other of the used wavelengths and if more than two wavelengths are used perform steps a) to f) for the remaining wavelengths one at a time.

One alternative way is to first perform steps a) to d) for one of the used wavelengths and then perform steps a) to d) for one other of the used wavelengths and if more than two wavelengths are used perform steps a) to d) for the remaining wavelengths one at a time. Thereafter, steps e) and f) may be performed in parallel for all of the used wavelengths. This alternative way increases the speed with which the method is carried out, i.e. decreases the time for carrying out the method.

In some embodiments of the method according to the present invention, two wavelengths are used, one covered by the wavelength range in which the specific molecules or structures used have a light absorption peak, and one wavelength outside said wavelength range, and wherein two cell analysis images are constructed for comparison.

In general it is sufficient to carry out the method using two different wavelengths, since then one image affected by the molecules or structures is obtained and one image unaffected by the molecules or structures is obtained. Thus, it is possible to compare the two images and detect the molecules or structures. By only using two wavelengths, the efficiency of the method is increased compared with using more than two wavelengths. However, by using more than two wavelengths the accuracy increases.

According to another specific embodiment of the method according to the present invention, the specific molecules or structures used shift the polarization direction of light, and wherein steps a) to f) are performed at least once without and at least once with the addition to step a) of shifting the polarization direction of the object beam and/or reference beam, thereby enabling comparison of said one and same at least one cell in images obtained in step f) and created by different polarization directions.

In this embodiment, at least one image where the polarization direction is shifted by the molecules or structures used is produced. When the polarization direction of the object beam or the reference beam is shifted, molecules or structures which in themselves shift the polarization direction randomized are visualized. By only shifting the polarization directions of the at least one object beam and/or the at least one reference beam so that they are perpendicular or substantially perpendicular to each other, and not having any molecules or structures which shift the polarization direction in themselves, a "zero image" not showing anything would be obtained. However, if molecules or structures are used which shift the polarization direction these will be shown in an image according to this specific embodiment of the present invention. As such, this is also a way of removing risk of uncertainties in relation to if you in fact are seeing molecules or structures stained or labelled to at least one cell or conjugated to antibodies which are bound either directly to said at least one cell or indirectly via another or several antibodies in a chain bound to said at least one cell.

It is important to realize that the expression "shifting the polarization direction of the at least one object beam and/or the at least one reference beam" does not include shifting both the at least one object beam and the at least one reference beam at the same time in a way which corresponds to creating an image without shifting the polarization directions of the at least one object beam and/or the at least one reference beam in relation to one another, i.e. going back to the initial position or a corresponding position before shifting the polarization directions.

According to one specific embodiment of the method according to the present invention, the specific molecules or structures used shift the polarization direction of light, and wherein steps a) to f) are performed at least once without and at least once with the addition to step a) of shifting the polarization direction of the at least one object beam and/or at least one reference beam so that the polarization directions of the at least one object beam and the at least one reference beam are perpendicular or substantially perpendicular to each other, thereby enabling comparison of said one and same at least one cell in images obtained in step f) and created by different polarization directions. The interest in having perpendicular polarization directions of the at least one object beam in relation to the at least one reference beam is further explained above.

One way to carry out the method involving performing steps a) to f) without and with the addition to step a) of shifting the polarization direction of the object beam and/or reference beam is to first perform steps a) to f) without the addition to step a) and then perform steps a) to f) including shifting the polarization direction of the at least one object beam and/or the at least one reference beam.

One alternative way is to first perform steps a) to d) without the addition to step a) and then perform steps a) to d) including shifting the polarization direction of the object beam and/or reference. Thereafter, steps e) and f) may be performed in parallel for the sequences of steps a) to d) performed without and with the addition to step a). This alternative way increases the speed with which the method is carried out, i.e. decreases the time for carrying out the method.

In some embodiments of the method according to the present invention, more than one type of molecules or structures are used and wherein at least one of the molecules or structures have a light absorption peak within a specific wavelength range and at least one of the molecules or structures shift the polarization direction of the at least one object beam of light and/or the at least one reference beam of light. In these embodiments molecules or structures having the ability to absorb light with a peak within a specific wavelength range are used together with molecules or structures having the ability to shift the polarization direction, i.e. two different types of molecules or structures are used. By combining these characteristics, it is possible to obtain both images created from light with different wavelengths and images created by different polarization directions. When having both these kinds of images, the certainty of the detection of the cell the molecules or structures are bound to is increased.

In some embodiments of the method according to the present invention, the specific molecules or structures used have a light absorption peak within a specific wavelength range and shift the polarization direction of the at least one object beam of light and/or the at least one reference beam of light. In these embodiments molecules or structures having both the ability to absorb light with a peak within a specific wavelength range and to shift the polarization direction are used, i.e. one type of molecules or structures are used. As said above, by combining these characteristics, it is possible to obtain both images created from light with different wavelengths and images created by different polarization directions. When having both these kinds of images, the certainty of the detection of the molecules or structures is increased and thus certainty of the detection of the cell the molecules or structures are bound to is increased.

In some embodiments of the method according to the present invention, two or more wavelengths are used, wherein at least one type of the specific molecules or structures used have a light absorption peak in a wavelength range covering at least one, but not all of the two or more wavelengths used, wherein the steps a) to f) are performed for each of the used wavelengths, and wherein at least one type of the specific molecules or structures used shift the polarization direction of light, wherein the steps a) to f) are performed at least once without and at least once with the addition to step a) of shifting the polarization direction of the at least one object beam and/or the at least one reference beam, thereby enabling comparison of said one and same at least one cell in images created from light with different wavelengths and by different polarization directions. In these embodiments, images created from light with different wavelengths and images created by different polarization directions are obtained. Thereby it is possible to analyze both these factors and thereby the certainty of the detection of the molecules or structures may be increased and the certainty of the detection of the cell the molecules or structures are bound to is increased. The minimum number of images produced in these embodiments of the method is three. One of these images may be a reference image obtained with a first wavelength and without the addition to step a). One of these images may be an image obtained using a second wavelength and without the addition to step a). One of these images may be an image obtained with the first wavelength, but with the addition to step a). However, in order to increase the accuracy of the method, both the number of images created from light with different wavelengths and images created by different polarization directions may be increased. Moreover, also in this case the shifting of the polarization direction of the at least one object beam and/or the at least one reference beam may be performed so that the polarization directions of the at least one object beam and the at least one reference beam are perpendicular or substantially perpendicular to each other.

The invention claimed is:

1. A method for detecting molecules or structures stained or labelled to at least one cell or conjugated to antibodies which are bound either directly to said at least one cell or indirectly via another or several antibodies in a chain bound to said at least one cell, the molecules or structures being capable of shifting the polarization direction of a beam of light, the method comprising using a digital holographic microscopy and imaging set up to detect the molecules or structures including the steps of:

performing digital holographic microscopy and imaging on a cell sample by
a) creating at least one object beam and at least one reference beam of light, where said at least one object beam and said at least one reference beam are mutually coherent;
b) shifting the polarization direction of the at least one object beam in relation to the at least one reference beam by shifting the polarization direction of the at least one object beam and/or the at least one reference beam;
c) exposing said cell sample to said at least one object beam, wherein the polarization direction of said at least one object beam is shifted by utilization of said molecules or structure;
d) superimposing said at least one object beam that has passed through said cell sample with said at least one reference beam and thereby creating an interference pattern;
e) detecting said interference pattern;
f) reconstructing phase and/or amplitude information of object wavefront from said interference pattern; and
g) constructing at least one cell analysis image for detection of molecules or structures stained or labelled to at least one cell or conjugated to antibodies which are bound either directly to said at least one cell or indirectly via another or several antibodies in a chain bound to said at least one cell.

2. The method according to claim 1, wherein the molecules or structures or the antibodies are bound to the cell surface of said at least one cell.

3. The method according to claim 1, wherein the molecules or structures have a light absorption peak within a specific wavelength range.

4. The method according to claim 1, wherein more than one type of molecules or structures are stained or labelled to at least one cell at the same place or places of said cell or conjugated to the same type of antibodies which are bound either directly to said at least one cell or indirectly via another or several antibodies in a chain bound to said at least one cell, and wherein at least one of the molecules or structures have a light absorption peak within a specific wavelength range and at least one of the molecules or structures shift the polarization direction of a beam of light used in the digital holographic microscopy and imaging setup.

5. The method according to claim 1, further comprising exposing said molecules or structures with light having at least two different wavelengths in comparison to one another.

6. The method according to claim 1, further comprising shifting the polarization direction of the at least one object beam of light and/or of the at least one reference beam of light used in the digital holographic microscopy and imaging setup so that the at least one object beam of light and the at least one reference beam of light obtain polarization directions which are perpendicular or substantially perpendicular to each other.

* * * * *